US00PP11972P2

(12) United States Plant Patent
Shank

(10) Patent No.: US PP11,972 P2
(45) Date of Patent: Jul. 3, 2001

(54) DRACAENA PLANT NAMED 'JANET CRAIG GOMEZII'

(76) Inventor: James E. Shank, 1601 NW. 97th Ave. Unit C-101 P.O. Box 025216, Miami, FL (US) 33102-5216

( * ) Notice: Subject to any disclaimer, the term of this patent is extended or adjusted under 35 U.S.C. 154(b) by 0 days.

(21) Appl. No.: 09/472,304

(22) Filed: Dec. 27, 1999

(51) Int. Cl.[7] ..... A01H 5/00
(52) U.S. Cl. ..... Plt./383
(58) Field of Search ..... Plt./383

(56) References Cited

U.S. PATENT DOCUMENTS

| | | | |
|---|---|---|---|
| P.P. 4,035 | 4/1977 | Obayashi | Plt./88 |
| P.P. 5,997 | 5/1987 | Krieser | Plt./88 |
| P.P. 6,346 | 10/1988 | Sandi-Matamoros | Plt./88 |
| P.P. 6,690 | 3/1989 | Browne | Plt./88 |
| P.P. 10,600 | 9/1998 | Janssen | Plt./8.811 |

*Primary Examiner*—Bruce R. Campell
*Assistant Examiner*—Susan B. McCormick
(74) *Attorney, Agent, or Firm*—James A. Lucas; Driggs, Lucas, Brubaker & Hogg Co., LPA

(57) ABSTRACT

A new and distinct cultivar of *Dracaena fragrans stednarii* characterized by its leaves having a richer dark green color, gently corrugated margins, and a broader width than those of its parent, and its cane having a color graduated from a brownish grey at the base to a green, partially smooth, surface at the tip.

3 Drawing Sheets

BACKGROUND OF THE INVENTION

The present invention relates to a new and distinct cultivar of a Dracaena plant, botanically known as *Dracaena fragrans stednerii* and known by the cultivar name Janet Craig Gomezzi. This plant is a sport of the parent *Dracaena fragrans stednerii*, which is unpatented stock that was introduced into Costa Rica from Central Africa. The new cultivar was discovered in 1995 by the inventor in Costa Rica, Central America, Province of Alajuela, District 11 Cutris; County No. 10 San Carlos. It was discovered as a naturally occurring sport in a cultivated area on an ornamental plant farm dedicated to cultivating *Dracaena fragrans stednerii*. The cultivar was reproduced by propagating it asexually using tip cuttings as well as top cuttings on the same ornamental plant farm where it was discovered.

The new cultivar grows faster than its parent. It has wider leaves than the leaves of the parent. It has leaves that are corrugated, whereas the leaves of the parent are not corrugated. The color of the exposed cane graduates from a brownish gray color at the base to rich green smooth surface at the top, whereas the exposed cane of the parent maintains a grayish brown color throughout its height.

The unique features of this new Dracaena plant are stable and have been reproduced through successive generations of asexual propagation.

The new Dracaena has not been observed under all possible environmental conditions. The phenotype may vary somewhat with variations in environment such as temperature, humidity, fertilization, day length and light intensity.

BRIEF SUMMARY OF THE INVENTION

The habit of growth is similar to the parent plant, growing about 6 feet overall the first year if allowed to grow without cutting. Because of the unique dark rich green color and mildly corrugated pattern of the leaf margins, this variety makes an excellent house plant. It propagates true from cuttings, rooting easily at nodes planted below the soil surface.

This cultivar is an ornamental cane marketed similarly to the parent and to *Dracaena fragrans massangeana* (Unpatented) the surface of which have an evenly brownish grey color. Contrasted to this is the cane surface of the new cultivar which graduates from the brownish grey color at the base to a partially smooth green surface at the top of the cane. The surface of this cane also differs from the cane surface of Dracaena 'Janet Craig' (Unpatented) which is somewhat uniformly green from the top to the base. The leaves of the new cultivar are broader than those of the parent and have a more pronounced, rich dark green color. The margins of the leaves are gently corrugated.

BOTANICAL DESCRIPTION

Figure 1:
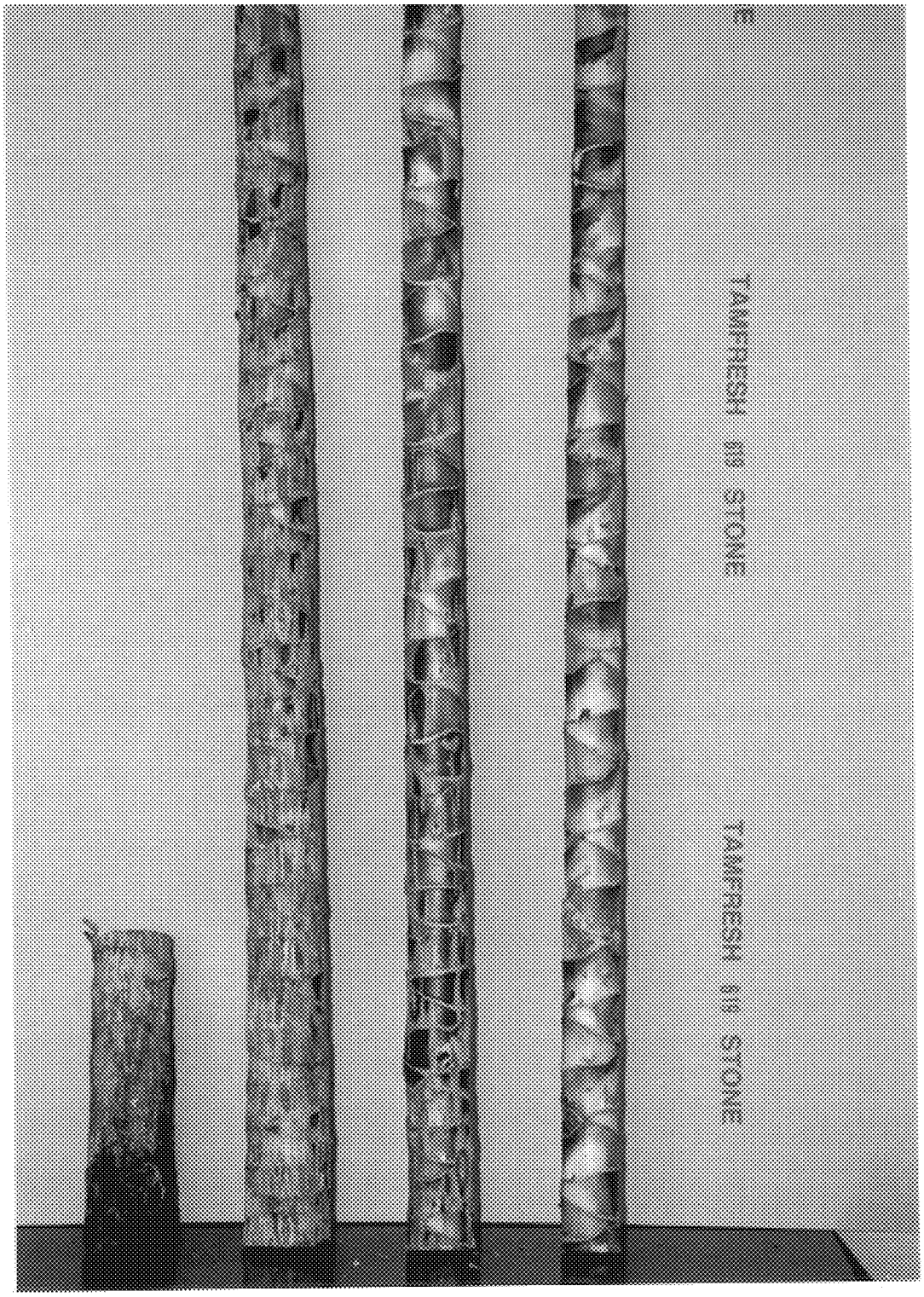
FIG. 1 shows a piece of cane about 3 years from planting of a tip that has been harvested and has been sectioned for viewing.
Figure 2:
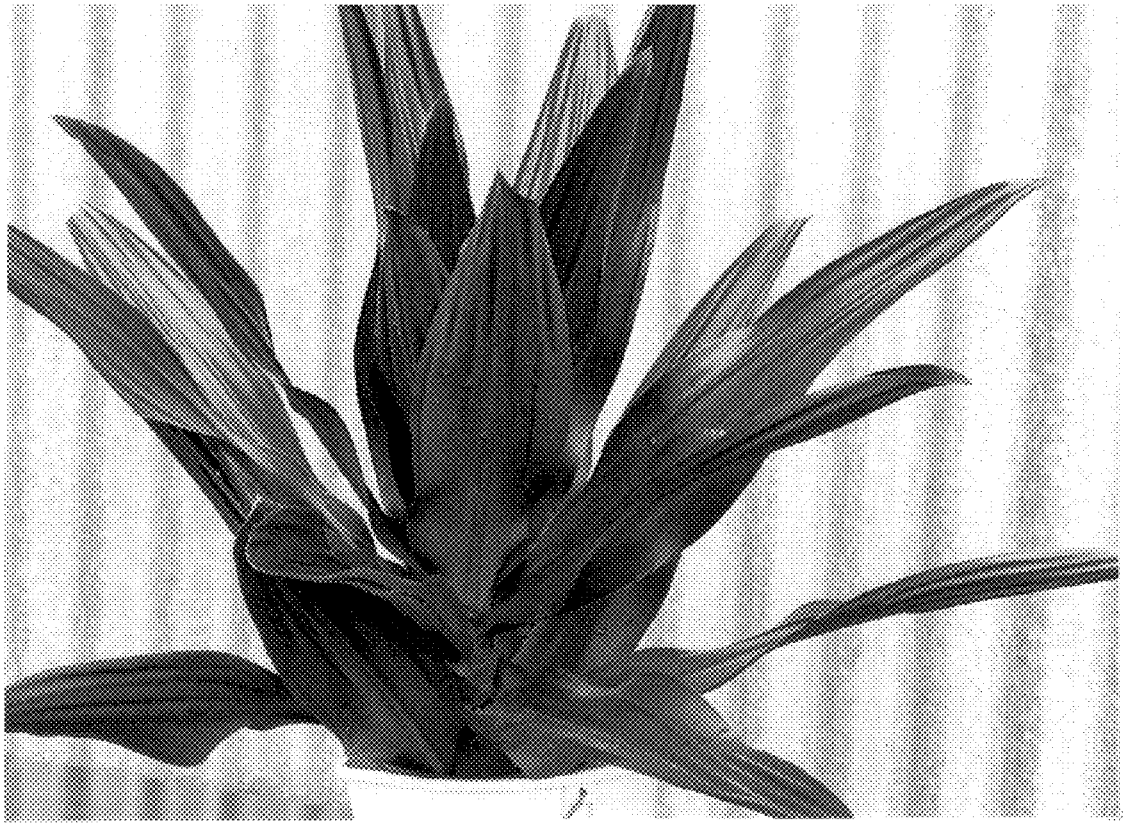
FIG. 2 is an elevation of the plant tip showing a close-up of the leaves of this new cultivar.
Figure 3:
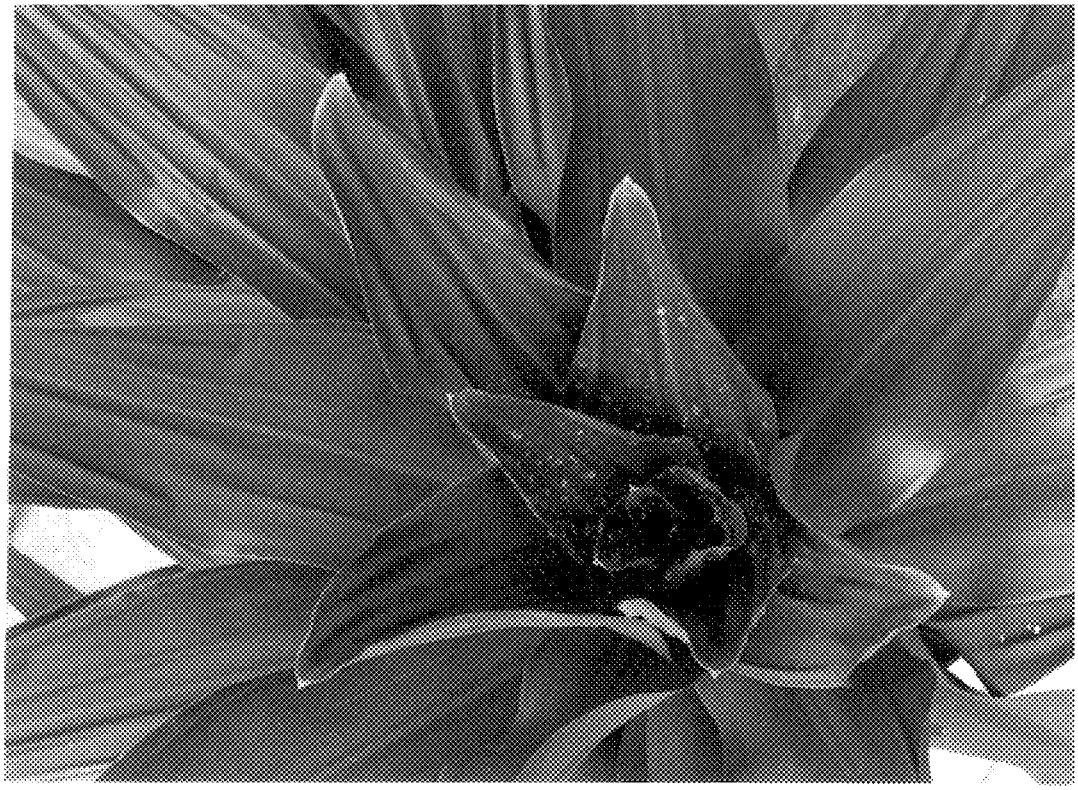
FIG. 3 is a top view of the plant tip.

Plant: herbaceous monocot.

*Age.*—The entire cane is 3 years old, and the tip of the cane is 24 months.

*Form.*—Cannoid (cane-like) of indeterminate monopodial growth.

*Once roots are established, growth rate.*—About 1 inch per week when grown in tropical lowlands approximately 125 meters above sea level. Tip, tops or cane all show root initiation readily within three weeks after planting directly in the soil or other rooting media.

Flowers: Neither the parent nor the sport have ever been observed to have flowered.

Stem:

*Size.*—50–60 mm in diameter.

*Internodal spacing.*—24–40 mm (average 34.9 mm).

*Epidermis.*—Chlorophyllous where exposed.

*Color.*—Grass green (British Colour Council), 28-F/7-8 Kornerup and Wanscher's Methuen Dictionary of Colour (K & W), 143B, Royal Horticultural Society Colour Chart — 1975 (RHS) at top of cane to RHS 199-D at base.

*Cuticle.*—Very refractive and papery in appearance; Very pale cinnamon RHS 164-D to silvery gray RHS 195-C.

Foliage:

*Leaves.*—Spirally arranged along stem with tightly adpressed leaf sheaths that envelop on average ⅔ of the circumference of the stem. Average number of leaves: 4.6 per every 10 cm. when measured on cane; 5.4 per every 10 cm. when averaged including the crown; Apex of cane more densely foliated due to compacted internodes, the apex having a rosette appearance. Medial and apical: shape: lanceolate, length: 36.0–45.0 cm. (average 41.95 cm.), width: 6.4–8.1 cm. (average 7.65 cm.) at middle length, laterally spreading, apical tuft somewhat erect, At apex, acute to subobtuse rarely acute — caudate; Base hastate, the auricles totally sheathing the stem and amplexicaulous; distance between auricles 7.5 cm. to 9.0 cm. (average 8.45 cm.), narrowing to a suprabasal constriction 3.2 cm. to 4.6 cm. wide (average 4.2 cm.); marginally subundulate, surficially subplicate, 3–4 plicae on each side of a central midvein Basal: length: shorter than medial and apical apically obtuse; color: 29F/7-8 (K & W), 143-B (RHS) texture: leaves are soft-leathery (subcoriaceous), pliable, smooth to the touch. The upper and lower leaf surface showns a slightly waxy or subpruinose 'bloom', especially toward the base.

Bud: at nodal meristem; shoots — single or multiple on same stem.

Disease resistance: normal for the species.

Cold hardiness: normal for the species.

Time from planting of cutting to market— about 3 years

I claim:

1. A new and distinct variety of *Dracaena frangrens stednerii* plant named 'Janet Craig Gomezii' as described and illustrated.

* * * * *